US00PP07852P

United States Patent [19]

Busey

[11] Patent Number: Plant 7,852

[45] Date of Patent: Apr. 7, 1992

[54] 'FX-10', A VARIETY OF ST. AUGUSTINEGRASS

[75] Inventor: Philip Busey, Plantation, Fla.

[73] Assignee: University of Florida, Gainesville, Fla.

[21] Appl. No.: 500,734

[22] Filed: Mar. 28, 1990

[51] Int. Cl.[5] ..... A01H 5/00
[52] U.S. Cl. ..... Plt./88
[58] Field of Search ..... Plt./88

*Primary Examiner*—James R. Feyrer
*Attorney, Agent, or Firm*—John R. Wetherell, Jr.

[57] ABSTRACT

A perennial, vegetatively propagated St. Augustinegrass genotype having resistance to the PDP southern chinch bug, resistance to seasonal drought, moderate resistance to gray leaf spot disease, sparse hairs on the adaxial surfaces of the young leaf blades, and bluish colored leaves.

5 Drawing Sheets

BACKGROUND OF THE INVENTION

This invention relates to a new and distinct perennial St. Augustinegrass genotype selected from among double-cross hybrids of parents introduced from Africa. The pedigree was (PI 290888×PI 293666)×(PI 300127×PI 300130) and the four parents were intercrossed by means of emasculation and controlled pollination. The selected hybrid genotype. FX-10, was propagated asexually at Fort Lauderdale by cutting stolons into segments containing at least one node, and planting them in soil, to increase planting stock for studying comparative performance with commercially available varieties. FX-10 is a distinct, asexually propagated variety of St. Augustinegrass.

SUMMARY OF THE INVENTION

FX-10 has resistance to the PDP southern chinch bug, to which Floratam is susceptible. FX-10 has resistance to seasonal drought and can be used for infrequently irrigated turf in a humid area such as southern Florida, where shallow subsurface soil moisture occurs. Compared with other varieties of St. Augustinegrass, FX-10 has moderate resistance to gray leaf disease and has bluish colored leaves. FX-10 has sparse hairs on the adaxial leaf blade surfaces. The adaptive advantages of FX-10 and its inflorescence and vegetative characteristics allow it to be distinguished from other St. Augustinegrasses. It maintains these traits when propagated asexually.

BRIEF DESCRIPTION OF THE VARIOUS FIGURES OF THE DRAWING

BOTANICAL DESCRIPTION OF THE CLAIMED PLANT

The following is a detailed description of the new grass variety, based upon observation of the plant grown under conventional greenhouse conditions, and in outdoor trays on raised benches and in field plots, with color notations based on *Munsell Book of Color: Glossy Finish Edition,* Munsell Color, Baltimore, Md., 1976; and *Munsell Color Charts for Plant Tissues,* Munsell Color, Baltimore, Md., 1977. Color descriptions were supplemented with names approximating the Munsell notations, the names described in Smith, *Naturalist's Color Guide,* The American Museum of Natural History, New York, N.Y., 1975.

FX-10 is a perennial, vegetatively propagated genotype of St. Augustinegrass (*Stenotaphrum secundatum* [Walt.] Kuntze). It grows by creeping or ascendant, dorsiventrally compressed stolons which root at the nodes. Vegetative dimensions and other vegetative characteristics of FX-10 are similar to Floratam, Bitterblue, and FX-33 in most respects and cannot be relied on for positive identification of samples. Stolon color of FX-10 is 5GY 6/6 (approximately parrot green) with 5RP 3/10 (approximately true purple) chromatic spots concentrated on the distal end of each internode. In mixture, the green and purple make the distal ends of internodes thus appear to the eye varying colors, depending upon the age of the plant and light conditions. In typical full sun conditions, the color of the ends of the internodes appears close to 2.5YR ¾ (approximately warm sepia). The development of purple chromatic spots can occur in most other parts of FX-10, especially the tips of the leaf blades, the exposed parts of the leaf sheaths, and the inflorescences. Blades are plicate, generally 25 to 285 mm long and 8 to 14 mm wide, abruptly contracted at the base, obtuse at the apex. Leaf dimensions of St. Augustinegrass genotypes vary greatly in response to age, light level, and other environmental factors. The ligule of FX-10 is a line of hairs. Leaf sheaths are laterally compressed.

Figure 1:
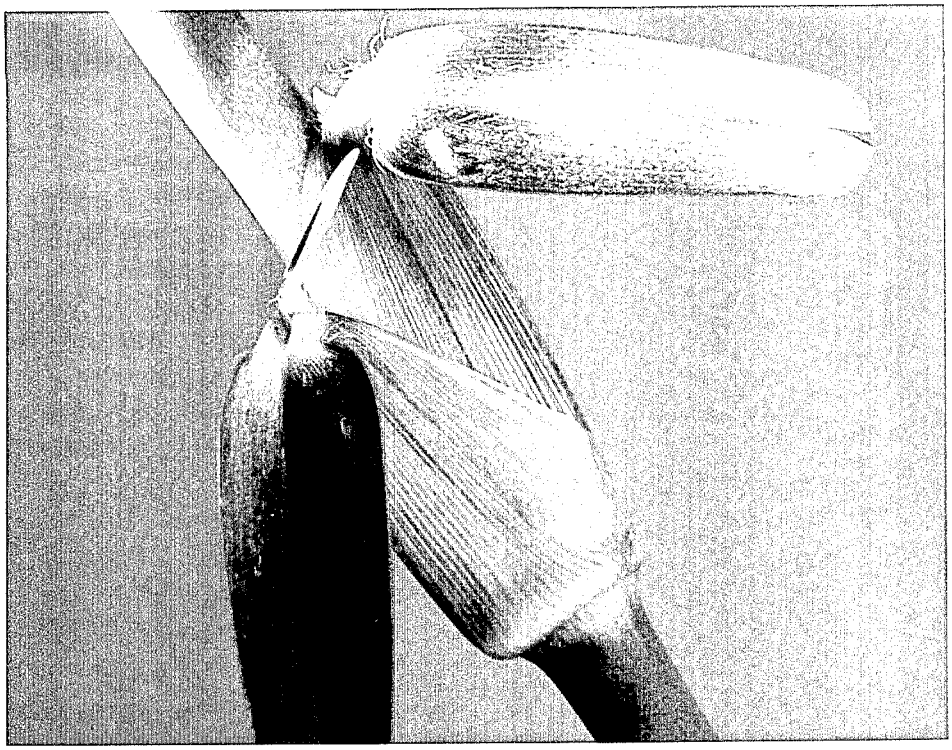
FIG. 1 shows the leaf blade adaxial surface of FX-10.
Figure 2:
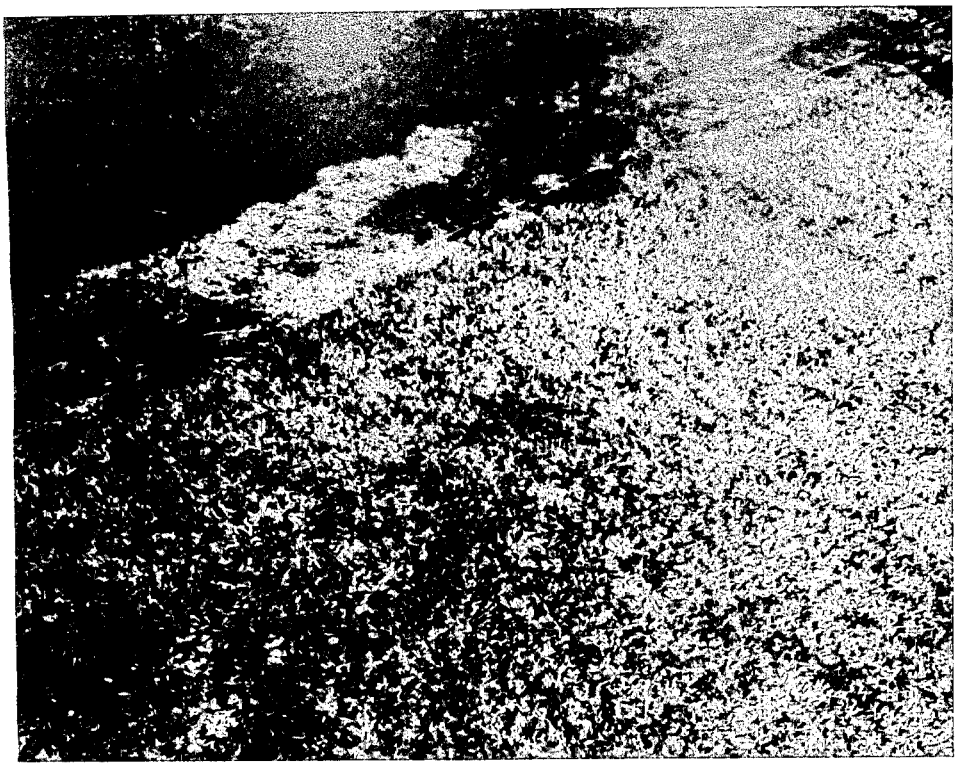
FIG. 2 shows the overall color appearance of a plot of FX-10 (lower right) compared to Jade (upper left).
Figure 3:
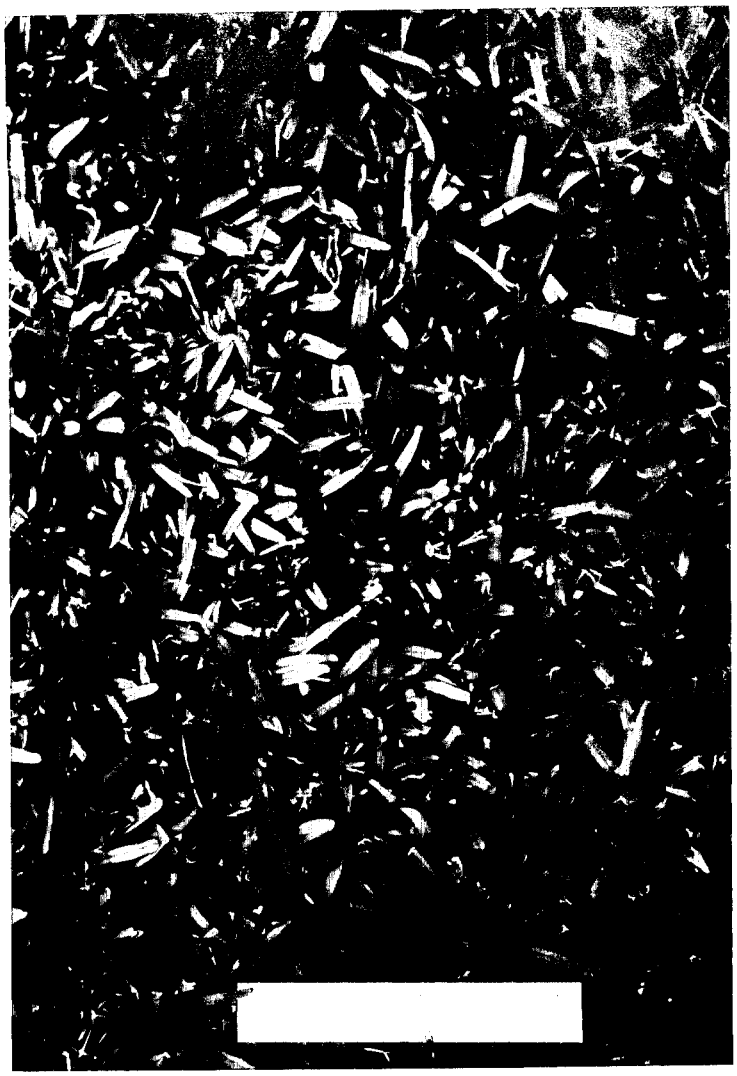
FIG. 3 shows the overall appearance of the leaf canopy of FX-10.

In contrast with most other cultivated varieties of St. Augustinegrass, FX-10 has hairs on both surfaces of the young leaf blades. The leaf hairs are sparsely distributed adaxially, averaging 21 per blade, and are even less frequent abaxially (Table 1). Hairs are 0.5 to 1 mm long and are discernible to the unaided eye by looking towards the base of the adaxial surface (FIG. 1). Except for FX-33, other recognized varieties of St. Augustinegrass have no hairs on the leaf blade surfaces, although hairs are present in all varieties on the ligule and collar region. When viewed from reflected light, adaxial leaf color of FX-10 typically varies between 7.5GY 5/4 (approximately grass green) and 7.5GY 4/4 under normal fertilization levels, thus leaf blades are more blue and less saturated than FX-33 (5GY 5/6, approximately parrot green). Leaf color of St. Augustinegrass genotypes varies in response to fertilization and other environmental factors, as well as the direction and quality of the light source. The overall color rating of FX-10, when viewed in a plot, is preferable to Bitterblue, Floratam, and FX-33 (Table 2). Compared with diploid varieties such as Jade, FX-10 is more bluish, less saturated, and lighter (FIG. 2). The overall vegetative appearance of FX-10 is represented in FIG. 3.

Figure 4:
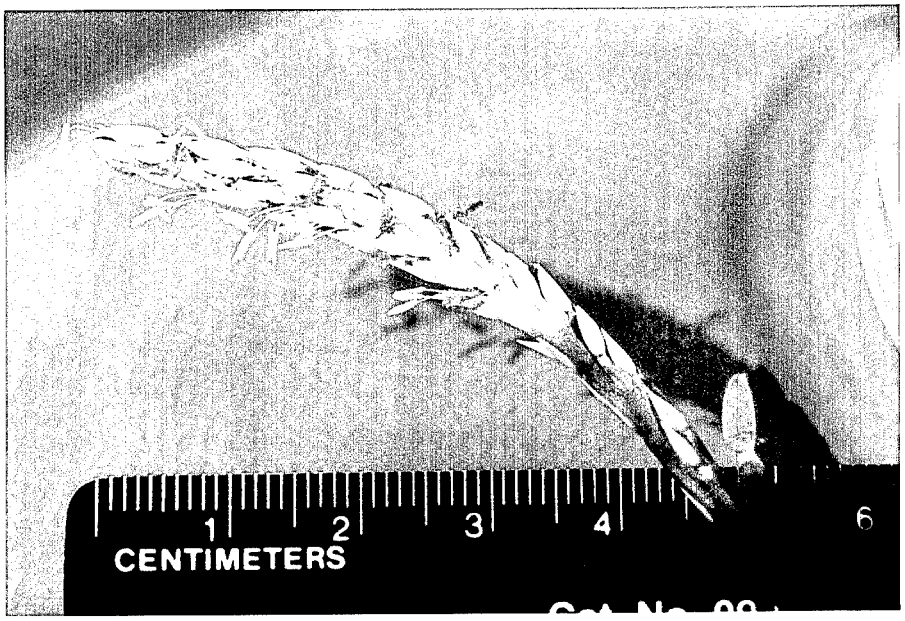
FIG. 4 shows the inflorescence of FX-10.

Inflorescences of FX-10 (FIG. 4) are terminal and axially, subtended by a flag leaf with reduced blade 7 to 25 mm long. The terminal inflorescences are dorsiventrally compressed spike-like panicles, with a floral region 50 to 90 mm long bearing 18 to 24 racemes embedded in pockets on one face of a corky main axis. Mean floral region length of FX-10, 76.3 mm, in shorter than that of Floratam, Floralawn, and FX-33, but similar to Bitterblue (Table 3). The non-flowering peduncle-like region below the floral region is extremely variable, 10 to 90 or more mm long. The axillary inflorescences are variable and much reduced in size compared with the terminal inflorescences. On terminal inflorescences, each raceme has 1 to 3 (occasionally 4) spikelets on an inconspicuous rachis.

Figure 5:
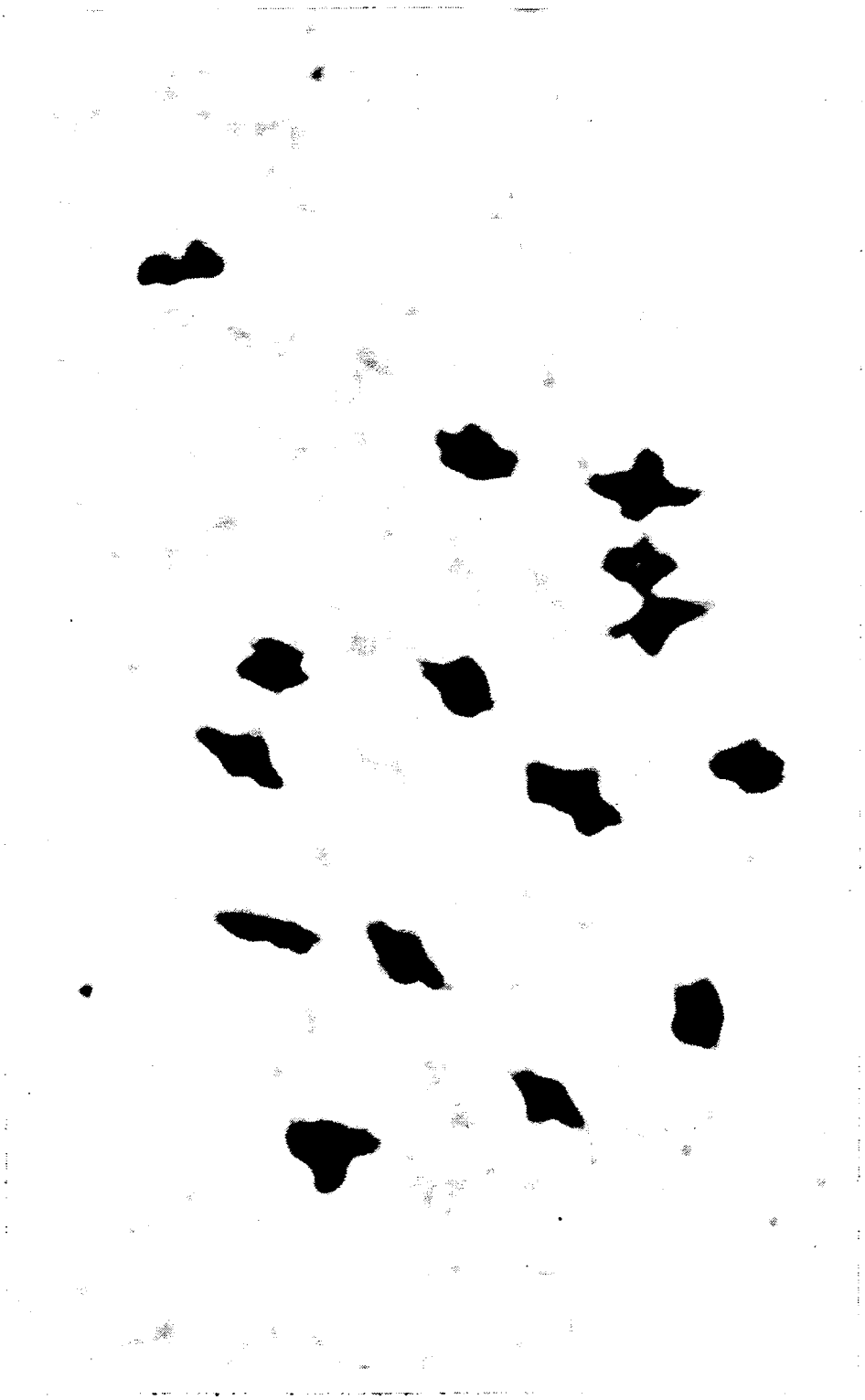
FIG. 5 shows a photomicrograph of the metaphase I chromosomes of FX-10, representing 15 bivalents (2n=30).

Spikelet length in St. Augustinegrass was shown to be adequately free of environmental effects for use in variety description and identification (Busey, *Crop Sci.*, 26:28, 1986). Spikelets of FX-10 are narrowly ovate, slightly acuminate, 4.1 to 5.0 mm long, about 1.8 mm wide, and awnless. Mean spikelet length of FX-10 is thus much shorter than Floratam and Floralawn which are >5.2 mm (Busey, ibid, 1986) (Table 3) and slightly shorter than Bitterblue and FX-33. Spikelets of FX-10 are longer than those of Breviflorus Race varieties (e.g., Raleigh and Seville), which are <4.4 mm. Glumes are membranaceous, the lower (and outer) glume truncate, 1 to 1.5 mm long, nerveless, the upper (and inner) glume about the full size of the spikelet and lemmas. The lower (and outer) floret is staminate, the upper (and inner) bisexual, its lemma with 5 to 7 longitudinal nerves and about equal in size to the spikelet. Genotype FX-10 has anther color 10YR 7/10 (approximately orange-buff), but anthers often vary from 10YR 7/12 (approximately deep chrome) to 2.5Y 7/10 (approximately apricot yellow). Stigma color is 5RP 3/10 (approximately true purple). The unreduced chromosome number of FX-10 is 2n=30 (Table 4). Chromosomes of FX-10 associate in diakinesis principally as bivalents (FIG. 5) with regular disjunction Busey, *Crop Sci.*, 30:588, 1990), while pairing and disjunction in Floratam are irregular (Busey, *Proc. Fla. Hort. Sci. Soc.*, 92:228, 1979). FX-10 differs from its female parent 290888-2 (=290888×293666) in having hairs on the leaves, but differs from its male parent in superior field quality rating. FX-10 differs from both parents in its reduced incidence of leaf spot disease (Table 5).

In southern Florida, FX-10 survives seasonal drought with nearly complete canopy coverage after 15 months without irrigation (Table 6). Under the same experimental conditions, the most widely grown variety of this region, Floratam St. Augustinegrass, shows severe loss of canopy coverage due to drought. The southern Florida region is subject to seasonal drought, due to seasonally variable rainfall and sand soils which have little water holding capacity. Nevertheless, this is a humid region and under experimental conditions where FX-10 has shown drought survival, there is a relatively shallow (1.4 m) aquifer and relatively shallow (0.6 m) zone of moist soil associated with a jagged rock substrate.

During drought, the duration permanent wilt of FX-10 is brief and is significantly less than Floratam (Table 6), thus FX-10 is most likely drought resistant by means of avoidance, rather than tolerance. It is not known to what degree the drought resistance of FX-10 is adequate for its survival with infrequent irrigation when it is grown in coastal ridges, central highlands, or sloped areas, which are drier than typical turf-covered areas of southern Florida. Furthermore, the quality of FX-10 is eventually severely damaged after years without irrigation. Turfgrass quality ratings of FX-10 are superior to Floratam but inferior to Bitterblue and FX-33 in a pre-stress establishment period under supplemental irrigation (Table 7). In year 1 without irrigation, FX-10 turf quality was superior to Floratam, slightly inferior to Bitterblue and FX-33, but nevertheless acceptable. In years 2 and 3 without irrigation, FX-10 turf quality was superior to FX-33 and Floratam. However, by year 3 the quality of FX-10 was unacceptable overall. While irigation would thus be necessary to maintain acceptable quality, FX-10 is usable as a sparingly irrigated turfgrass in southern Florida. In a Fort Lauderdale research lawn planted with FX-10 St. Augustinegrass, I have found that five irrigations between July 1990 and March 1991 (9 months) were more than adequate to maintain acceptable turf quality. (Of the five irrigations, four were applied primarily to wash in fertilizer.) Southern Florida is an important region for growing turfgrass, and primarily St. Augustinegrass lawns are used by nearly 5 million inhabitants. The usefulness of a non-irrigated variety of St. Augustinegrass could be large.

FX-10 is resistant (Busey, *Crop Sci.*, 30:588, 1990) to the PDP (Polyploid Damaging Popluation, Busey and Center, *J. Econ. Ent.*, 80:608, 1987) southern chinch bug which has damaged Floratam in Florida since 1985 (Table 8). In the same laboratory tests, Floratam was susceptible to the PDP southern chinch bug, based on high fecundity and extended survival of PDP southern chinch bugs on Floratam. The resistance of FX-10 to PDP southern chinch bugs has been verified in the field (Table 8), while Floratam plots in the same trial were severely destroyed. The resistance of FX-10 to the PDP southern chinch bug is useful, because the southern chinch bug is the most important insect pest of St. Augustinegrass in Florida, and has damaged Floratam in 37 counties of Florida.

FX-10 has moderate resistance to gray leaf spot disease, evidenced by much reduced leaf spot damage ratings compared with Bitterblue, Floratam, and FX-33 (Table 5 and 9). Unlike FX-33 which displays variable and sometimes severe leaf spotting in sand soil (e.g., July 1989, Table 9), FX-10 is consistently less damaged across varying locations and seasons. FX-10 has slower coverage than other varieties, such as Bitterblue, Floratam, and FX-33, but achieves a higher apparent density during production, compared with Bitterblue and Floratam (Table 10). FX-10 is more prone to weed infestation than Floratam. FX-10 shows less damage due to atrazine herbicide than FX-33, but more damage than Floratam, when all are treated in a sandy soil (Table 10). FX-10 provides superior quality ratings compared with FX-33, Floratam, and Bitterblue, when all were subjected to moderate (73%) artificial shade stress (Table 11).

TABLE 1

Pubescence on leaves of FX-10 and other St. Augustinegrasses[1]

| Selection/variety | Adaxial surface (hairs/leaf) | Abaxial surface (hairs/leaf) |
|---|---|---|
| FX-10 | 21 ± 16 | 12 ± 7 |
| FX-33 | 51 ± 23 | 219 ± 42 |
| Bitterblue | 0 | 0 |
| Delmar (Scotts 6-72-99) | 0 | 0 |
| Floralawn (FA-108) | 0 | 0 |
| Floratam (FA-110) | 0 | 0 |
| Floratine (FA-20) | 0 | 0 |
| Florida Common | 0 | 0 |
| Jade (Scotts 6-72-182) | 0 | 0 |
| Raleigh (NCSA-21) | 0 | 0 |
| Seville (Scotts 6-68-516) | 0 | 0 |
| Sunclipse (Scotts 6-72-130) | 0 | 0 |

[1]Based on five or more leaves of each selection/variety. Values following the ± symbol are standard errors of the means.

TABLE 2

Color rating of FX-10 and other St. Augustinegrasses[1]

| | February, 1989[2] | July, 1989[3] |
|---|---|---|
| FX-10 | 9.3 ± 0.2 | 8.7 ± 0.2 |
| FX-33 | 6.9 ± 0.2 | 6.9 ± 0.2 |
| Floratam | 7.3 ± 0.3 | 7.7 ± 0.1 |
| Bitterblue | 7.2 ± 0.3 | 7.9 ± 0.3 |

[1]Rating 10 = most preferred color; 1 = least preferred color. Values following the ± symbol are standard errors of the means.
[2]Field planting, LaBelle, Florida. Planted: May 1988.
[3]Field planting, Fort Lauderdale, Florida. Planted: August 1987.

TABLE 3

Inflorescence characteristics of FX-10 and other St. Augustinegrasses[1]

| Selection/variety | Spikelet length (mm) | Glume length (mm) | Floral region length (mm) |
|---|---|---|---|
| FX-10 | 4.49 ± 0.04 | 1.17 ± 0.04 | 76.3 ± 4.9 |
| FX-33 | 5.09 ± 0.09 | 0.98 ± 0.03 | 115.6 ± 6.0 |
| Bitterblue | 4.96 ± 0.06 | 1.11 ± 0.07 | 84.0 ± 2.2 |
| Floralawn | 5.76 ± 0.08 | 1.59 ± 0.06 | 105.6 ± 4.6 |
| Floratam | 5.74 ± 0.10 | 1.75 ± 0.07 | 129.2 ± 5.0 |
| Raleigh | 4.23 ± 0.07 | 1.55 ± 0.05 | 63.0 ± 1.7 |
| Seville | 4.22 ± 0.07 | 1.10 ± 0.09 | 73.0 ± 1.7 |

[1]Nursery trays, Fort Lauderdale, Florida. Data: July, 1989. Values following the ± symbol are standard errors of the means.

TABLE 4

Anther color, stigma color, and chromosome number of FX-10 and other St. Augustinegrasses.

| Selection/variety | Anther color | Stigma color | Chromosome number |
|---|---|---|---|
| FX-10 | 10YR 7/10[1] | 5RP 3/10[1] | 30 |
| FX-33 | 10YR 7/12 | 5RP 3/10 | 30 |
| Delmar | — | White[2] | 18 |
| Floralawn | 10YR 7/12 | 5RP 3/10 | — |
| Floratam | 10YR 7/12 | 5RP 3/10 | 32[4] |
| Bitterblue | 10YR 7/12 | 5RP 3/10 | — |
| Floratine | 10YR 7/12 | 5RP 3/10 | 27 |
| Florida Common | — | — | 18 |
| Jade | — | — | 18 |
| Roselawn | 10YR 7/12 | 5RP 3/10 | 18 |
| Raleigh | 2.5Y 8/8 | White[2] | 18 |
| Seville | 2.5Y 8/8 | Bicolor[3] | 18 |

[1]Based on undehisced, newly emerged anthers.
[2]The stigma of Delmar and Raleigh appears white, even though it is translucent and without pigment. This is because the microscopic structure of the branches creates a diffused gloss.
[3]White stigma branch tips and purple stigma branch bases.
[4]The chromosome number of Floratam is based on an average of tapetal cells, which are more stable than microsporocytes (Busey, Proc. Fla. State Hort. Soc., 92:228, 1979), but are still subject to an observed range from 30 to 34, which is not explained.

TABLE 5

Leaf spot rating, visual leaf hairiness rating, and visual quality ratings of FX-10, its antecedents, and named cultivars

| Selection/variety | Relation | Leaf spot rating[1] | Hairiness[2] | Visual quality rating[3] Year 1[4] | Visual quality rating[3] Year 2[5] |
|---|---|---|---|---|---|
| FX-10 | Progeny | 5.0 ± 0.0 | 3.0 ± 0.0 | 4.8 ± 0.5 | 7.5 ± 1.0 |
| 290888-2 | Female parent | 7.0 ± 0.0 | 1.0 ± 0.0 | 5.3 ± 2.1 | 6.8 ± 2.8 |
| 300127-8 | Male parent | 9.3 ± 0.3 | 4.0 ± 0.0 | 4.1 + 0.9 | 4.5 ± 1.0 |
| FX-33 | Cultivar | 8.3 ± 0.8 | 4.5 ± 0.5 | 4.9 ± 0.4 | 5.8 ± 2.3 |
| Bitterblue | Cultivar | 8.1 ± 0.4 | 1.0 ± 0.0 | 3.1 ± 0.3 | 3.8 ± 0.5 |
| Floratam | Cultivar | 7.0 ± 0.4 | 1.0 ± 0.0 | 5.3 ± 0.4 | 5.6 ± 0.9 |

[1]Rating 1 = no spots; 10 = severe spots. Values following the ± symbol are standard errors of the means. Field data Fort Lauderdale, Florida, August 1984; field area planted June 1984.
[2]Rating 1 = no hairs; 5 = very hairy; evaluated December 1984; same field areas as above.
[3]Rating 10 = best possible, 1 = dead; same field area as above.
[4]Mean of ratings taken August and December 1984 and February and May 1985.
[5]Mean of ratings taken September 1985 and March 1986.

TABLE 6

Pre-stress and post-stress canopy coverage, and duration permanent wilt of FX-10 and other St. Augustinegrasses, associated with withholding irrigation during a seasonal drought[1]

| Selection/variety | Canopy coverage: Pre-stress (%) | Canopy coverage: Post-stress (%) 2 mos. (%) | Canopy coverage: Post-stress (%) 15 mos. (%) | Duration permanent wilt (days) |
|---|---|---|---|---|
| FX-10 | 90 ± 4 | 98 ± 1 | 95 ± 4 | 2.5 ± 2.0 |
| FX-33 | 99 ± 1 | 99 ± 1 | 94 ± 3 | 0.8 ± 0.5 |
| Floratam | 97 ± 2 | 36 ± 9 | 43 ± 11 | 21.5 ± 1.6 |
| Bitterblue | 99 ± 1 | 97 ± 2 | 93 ± 5 | 6.3 ± 2.9 |

[1]Field planting, Fort Lauderdale, Florida. Planted: August 1987. Data: March 1988 through June 1989. During March and the first part of April 1988 (41 days) only 32 mm rain was received, which was followed by a period of adequate rainfall, and subsequent dry months. Values following the ± symbol are standard errors of the means.
[2]Permanent wilt was observed as a plot which remained wilted in the morning (0800 hours); its duration was observed as a period of continuous permanent wilt, until a resumption of rain.

TABLE 7

Turfgrass quality ratings of FX-10 and other St. Augustinegrasses[1]

| Selection/variety | Pre-stress[2] | During stress[3] Year 1 (1988) | During stress[3] Year 2 (1989) | During stress[3] Year 3 (1990) |
|---|---|---|---|---|
| FX-10 | 6.8 ± 0.2 | 7.1 ± 0.3 | 7.6 ± 0.4 | 5.9 ± 0.6 |
| FX-33 | 7.7 ± 0.1 | 7.6 ± 0.1 | 6.5 ± 0.4 | 3.3 ± 0.3 |
| Floratam | 6.0 ± 0.3 | 3.9 ± 0.4 | 3.8 ± 0.5 | 4.6 ± 0.5 |
| Bitterblue | 7.5 ± 0.3 | 7.7 ± 0.3 | 6.9 ± 0.4 | 5.1 ± 0.6 |

[1]Field planting, Fort Lauderdale, Florida. Planted: August 1987. Turfgrass quality rated on a 1 to 10 scale, with 10 = best, 1 = worst, and 7 = acceptable. Values following the ± symbol are standard errors of the means.
[2]Data: December 1987 and February 1988, mean of two dates of evaluation.
[3]Data: April 1988 through December 1990, mean of nine, twelve, and seven monthly evaluations during 1988, 1989, and 1990, respectively.

TABLE 8

Longevity, oviposition rate, and reproduction of adult PDP southern chinch bugs confined on FX-10 and other St. Augustinegrasses, and field damage

| Selection variety | Confinement data[1] Longevity (days) | Confinement data[1] Oviposition rate (eggs/female/week) | Confinement data[1] Reproduction (eggs/female/lifetime) | Host suitability | Field damage[2] (% of canopy dead) |
|---|---|---|---|---|---|
| FX-10 | 29.9 ± 4.0 | 3.8 ± 0.7 | 14 ± 4 | Resistant | 0 ± 0 |
| FX-33 | 21.2 ± 4.1 | 2.7 ± 0.5 | 7 ± 2 | Resistant | 5 ± 5 |
| Bitterblue | — | — | — | Susceptible | 90 ± 7 |

TABLE 8-continued

Longevity, oviposition rate, and reproduction of adult PDP southern chinch bugs confined on FX-10 and other St. Augustinegrasses, and field damage

| | Confinement data[1] | | | | |
|---|---|---|---|---|---|
| Selection variety | Longevity (days) | Oviposition rate (eggs/female/week) | Reproduction (eggs/female/lifetime) | Host suitability | Field damage[2] (% of canopy dead) |
| Floratam | 45.4 ± 6.1 | 11.5 ± 1.0 | 65 ± 17 | tible Susceptible | 78 ± 13 |

[1]Means of 18 pairs (one male and one female) of laboratory colony PDP southern chinch bugs per selection/variety. Values following the ± symbol are standard errors of the means. All bugs were maintained by replacing grass food sources each week for the natural lifetime of the bugs.

[2]Field planting, LaBelle, Florida. Planted: May 1988. Data: November 1990.

TABLE 9

Leaf spot rating of FX-10 and other St. Augustinegrasses[1]

| | November, 1987[2] | July, 1989[2] | July, 1988[3] |
|---|---|---|---|
| FX-10 | 1.6 ± 0.3 | 3.6 ± 0.4 | 3.8 ± 0.3 |
| FX-33 | 2.3 ± 0.3 | 6.9 ± 0.4 | 3.9 ± 0.4 |
| Floratam | 4.5 ± 0.6 | 6.4 ± 0.2 | 4.8 ± 0.4 |
| Bitterblue | 4.1 ± 0.4 | 6.5 ± 0.6 | 5.7 ± 0.3 |

[1]Rating 1 = no spots; 10 = severe spots. Values following the ± symbol are standard errors of the means.

[2]Field planting, Fort Lauderdale, Florida. Planted: August 1987.

[3]Field planting, LaBelle, Florida. Planted: May 1988.

TABLE 10

Production characteristics of FX-10 and other St. Augustinegrasses

| | Cover (3 mos.)[1] (%) | Lateral stolon Extension[2] | Density[2] | Weed infestation[3] | Atrazine damage[4] |
|---|---|---|---|---|---|
| FX-10 | 34.4 ± 2.9 | 6.9 ± 0.2 | 7.7 ± 0.2 | 33 ± 14 | 24.2 ± 7.6 |
| FX-33 | 65.0 ± 9.1 | 7.1 ± 0.3 | 7.5 ± 0.3 | 41 ± 12 | 91.3 ± 3.7 |
| Floratam | 66.3 ± 9.3 | 9.5 ± 0.2 | 3.3 ± 0.2 | 6 ± 3 | 12.5 ± 5.7 |
| Bitterblue | 66.9 ± 6.3 | 8.0 ± 0.2 | 5.2 ± 0.2 | 23 ± 7 | 41.7 ± 9.7 |

[1]Field planting, Fort Lauderdale. Planted: August 1987. Data: November 1987.
[2]Field planting, LaBelle, Florida. Planted: May 1988. Data: July 1988. Spread and density rated on a 1 to 10 scale, with 10 = greatest, 1 = least.
[3]Percent canopy. Field planting, LaBelle, Florida. Planted May 1988. Data: July 1990.
[4]Percent of lost canopy. Field planting, LaBelle, Florida. Planted: May 1988. Data: May 1989.

TABLE 11

Turfgrass quality ratings of FX-10 and other St. Augustinegrasses rated under 73% artificial shade[1]

| | Turfgrass quality |
|---|---|
| FX-10 | 8.1 ± 0.2 |
| FX-33 | 6.6 ± 0.3 |
| Floratam | 6.4 ± 0.2 |
| Bitterblue | 5.2 ± 0.3 |

[1]Field planting, Fort Lauderdale, means of four dates of evaluation. Planted: March 1989. Data: June and July 1989. Turfgrass quality rated on a 1 to 10 scale, with 10 = best, 1 = worst, and 7 = acceptable. Values following the ± symbol are standard errors of the means.

I claim:

1. A new and distinct variety of St. Augustinegrass, substantially as herein illustrated and described, characterized by its distinctive combination of inflorescence and vegetative characteristics, its superior resistance to seasonal drought when grown in a humid region with shallow subsurface soil moisture, its moderate resistance to gray leaf spot disease, its bluish colored foliage, and its resistance to the PDP southern chinch bug.

* * * * *